United States Patent
Kessler et al.

(10) Patent No.: US 12,241,881 B2
(45) Date of Patent: Mar. 4, 2025

(54) PARTICULATE-BASED CUMULATIVE CONTAMINANT SAMPLING DEVICE

(71) Applicant: UNITED STATES GEOLOGICAL SURVEY, Reston, VA (US)

(72) Inventors: Samuel C. Kessler, Campbellsville, KY (US); Peter J. Cinotto, Shelbyville, KY (US)

(73) Assignee: U.S. Geological Survey, Reston, VA (US)

( * ) Notice: Subject to any disclaimer, the term of this patent is extended or adjusted under 35 U.S.C. 154(b) by 567 days.

(21) Appl. No.: 17/531,292

(22) Filed: Nov. 19, 2021

(65) Prior Publication Data

US 2023/0168235 A1    Jun. 1, 2023

(51) Int. Cl.
| | | |
|---|---|---|
| *G01N 33/18* | (2006.01) | |
| *G01N 1/04* | (2006.01) | |
| *G01N 1/40* | (2006.01) | |
| *G01N 5/00* | (2006.01) | |

(52) U.S. Cl.
CPC ............. *G01N 33/18* (2013.01); *G01N 1/04* (2013.01); *G01N 1/4005* (2013.01); *G01N 1/4077* (2013.01); *G01N 5/00* (2013.01); *G01N 2001/4083* (2013.01)

(58) Field of Classification Search
CPC ........ G01N 33/18; G01N 1/04; G01N 1/4005; G01N 1/4077; G01N 5/00; G01N 2001/4083; G01N 1/12
USPC ....................................................... 73/61.41
See application file for complete search history.

(56) References Cited

U.S. PATENT DOCUMENTS

| | | | | |
|---|---|---|---|---|
| 3,890,290 A * | 6/1975 | McCabe | ................ | B01D 46/02 |
| | | | | 210/136 |
| 7,430,929 B1 * | 10/2008 | Vroblesky | ................ | E02D 1/06 |
| | | | | 73/864.74 |
| 8,578,797 B2 * | 11/2013 | Zeng | ........................ | E02D 1/06 |
| | | | | 73/864.74 |
| 11,131,609 B2 * | 9/2021 | Hanhauser | ................ | C02F 1/42 |

(Continued)

FOREIGN PATENT DOCUMENTS

JP          H11147008 A   *   6/1999

OTHER PUBLICATIONS

Cornman RS, McKenna JE Jr, Fike J, Oyler-McCance SJ, Johnson R. 2018. An experimental comparison of composite and grab sampling of stream water for metagenetic analysis of environmental DNA. PeerJ 6:e5871 DOI 10.7717/peerj.5871 (Year: 2018).*

(Continued)

*Primary Examiner* — Marrit Eyassu
(74) *Attorney, Agent, or Firm* — James Mitchell

(57) ABSTRACT

In one embodiment, a sampling device includes: an elongated tubular body having a longitudinal axis and a hollow interior enclosed at a top longitudinal end and a bottom longitudinal end of the body and a particulate matter. One or more mesh bags are disposed in the interior of the body and configured to contain the particulate matter inside a first mesh bag. The first mesh bag is an innermost mesh bag contained inside one or more outer mesh bags in a nested configuration when two or more mesh bags are disposed in the interior of the body. The body includes a plurality of body openings on one half lateral side of the body and no body openings on an opposite half lateral side of the body.

23 Claims, 9 Drawing Sheets

(56) References Cited

U.S. PATENT DOCUMENTS

| | | | | |
|---|---|---|---|---|
| 2011/0126644 A1* | 6/2011 | Hayes | ................... | G01N 1/10 |
| | | | | 210/232 |
| 2012/0073806 A1* | 3/2012 | Barrows | ................ | E21B 49/08 |
| | | | | 166/264 |
| 2021/0354055 A1* | 11/2021 | Gupta | ................ | G01N 1/4077 |

OTHER PUBLICATIONS

Kessler, "Misdiagnosing Our Water Quality? A Cumulative Water-Sampling Method Suggests Need for New Standards in the United States", Published in Grawemeyer Colloquium Papers, vol. 2020 [2021], 3 pages.

Cinotto, "Occurrence of Fecal-Indicator Bacteria and Protocols or Identification of Fecal-Contamination Sources in Selected Reaches of the West Branch Brandywine Creek", Published in Chester County, Pennsylvania, Scientific Investigations Report 2005-5039, U.S. Department of the Interior, U.S. Geological Survey (2005), 99 pages.

Nix et al.,"Use of Sediment Bags as a Monitor of Fecal Pollution in Streams, Bulletin of Environmental Contamination and Toxicology", 45:864-869 (1990), 6 pages.

Nix et al.,"Fecal Pollution Events Reconstructed and Sources Identified Using a Sediment Bag Grid, Water Environment Research", 66:6, 814-818 (1994), 6 pages.

Pachepsky et al., "*Escherichia coli* and Fecal Coliforms in Freshwater and Estuarine Sediment, Critical Reviews in Environmental Science and Technology", 41:12, 1067-1110 (2011), 45 pages.

\* cited by examiner

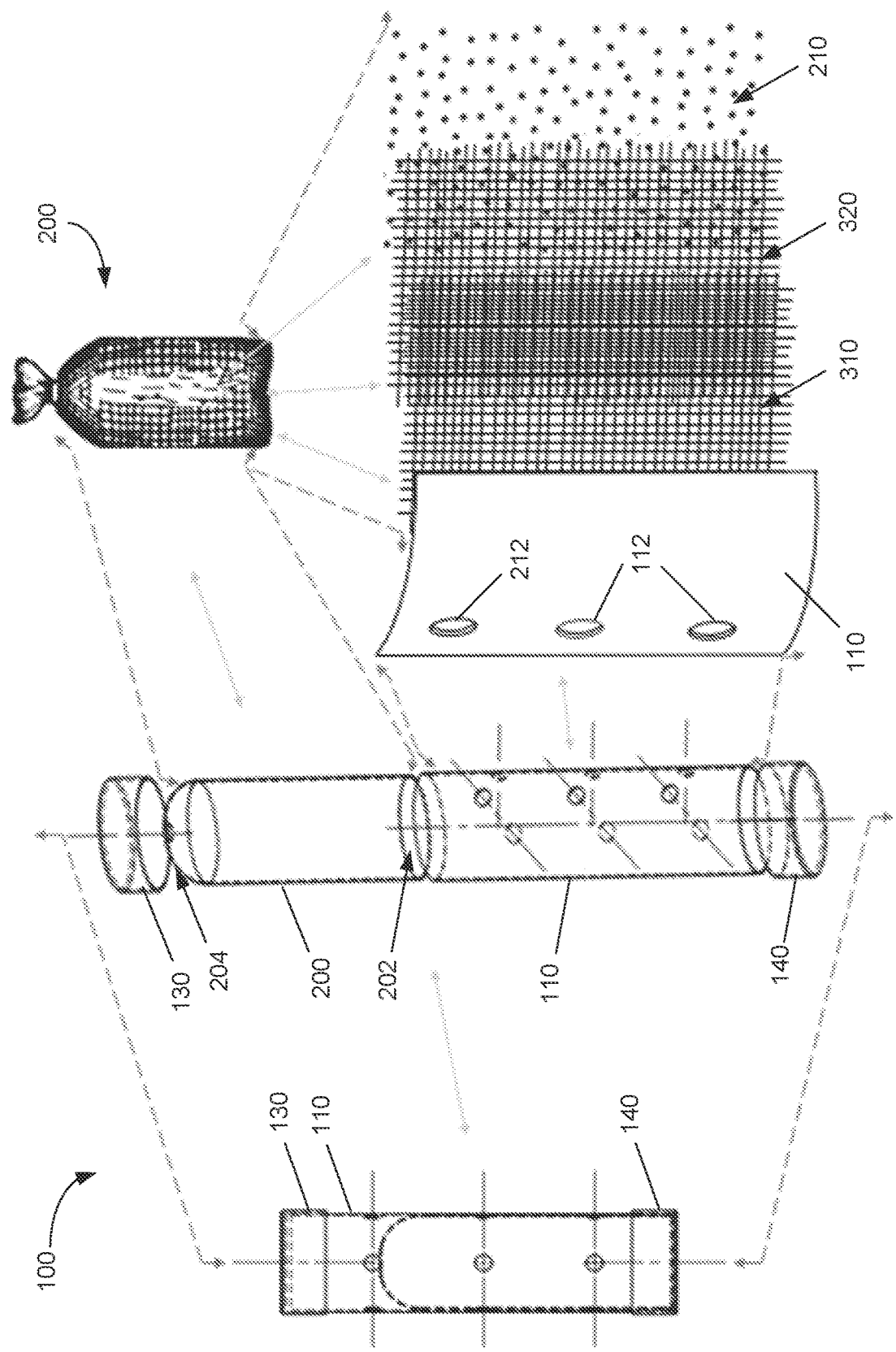

PARTICULATE-BASED CUMULATIVE CONTAMINANT SAMPLING DEVICE

STATEMENT OF GOVERNMENT INTEREST

The invention described herein was made in part by one or more employees of the United States Government, Department of the Interior, and may be manufactured and used by or for the Government of the United States of America for governmental purposes without the payment of any royalties thereon or therefore.

BACKGROUND

Field of the Invention

The present invention relates to apparatus and methods of sampling or screening of water quality and, more specifically, by cumulative sampling through screening of water quality by capturing contaminants over time in a volume of diatomaceous earth, or other similar particulate matter, held within a device.

Description of the Related Art

This section introduces aspects that may help facilitate a better understanding of the invention and differentiation from art that one may consider related. Accordingly, the statements of this section are to be read in this light and are not to be understood as admissions about what is prior art or what is not prior art.

Across the world, it is estimated that 4.5 billion people live near water sources "impaired" for use or contact. Standards for human interaction with the water sources are established by international organizations such as the WHO (World Health Organization), and legislative bodies from national to local levels with jurisdiction over the quality of the waterways to ensure public and environmental health. Standards are often assessed from "grab samples" of water taken from a waterbody at a certain time using a sterile jar, bag, or similar vessel, with a minimum number analyzed. These samples are used to assess Total Maximum Daily Loads (TMDLs) of a targeted contaminant. Once the TMDL is reached, States and local governments may shut down beaches or suspend water usage from the contaminated sources, for instance.

Grab sampling of water from the respective river, stream, or lake is the most commonly accepted testing method by the U.S Environmental Protection Agency to assess Total Maximum Daily Loads (TMDLs) for surface-water quality across the United States. Grab sampling tests water and soil at a specific location and time. However, the source of the TMDL contaminant cannot be readily identified with grab sampling as it does not provide data across time and (or) various flow conditions. Because grab sampling is typically performed at specific locations at discrete points in time, the methodology can be quite costly and can only produce discrete sampling data that may not be sufficiently informative and, as such, may be of limited use.

SUMMARY

An embodiment of the present invention is a cumulative sampling device developed to provide a quick and cost-effective method to help identify source(s) of targeted contaminants including fecal-indicator bacteria such as *E. coli* bacteria.

This allows entities to effectively determine potential source locations of targeted contaminants with a device that is easily deployable and that can be tested onsite, allowing for targeted mitigation activities with minimal cost.

Under cumulative sampling, a container with a substrate, such as diatomaceous earth or similar sand-like particles, is placed in a body of water. Targeted contaminants that attach or grow on the substrate are collected and then analyzed to yield information on contamination. Water filled within the container form a water column for cumulative sampling.

The cumulative sampling methods of prior mention were studied using sediment bags in the 1990's. These original sediment-bag studies found direct linear correlation with grab-sampled *E. coli* in a lab setting and demonstrated sediment bags as more effective at contaminant tracing in the field. Drawbacks to the method included particle loss to flows and inability to function in low flow, and lack of correlation with grab sampling in outdoor natural stream settings. The present invention overcomes these drawbacks by providing embodiments of a sampling device that avoid or at least significantly reduce particle loss increasing accuracy of tests, and are able to function in zero, low as well as high flow, and can be combined with grab sampling in outdoor natural stream settings to collect contaminant data to identify locations of contaminant growth and source of contaminant growth.

Embodiments of the present invention provide a cumulative sampling device with diatomaceous earth (DE), or similar fine particulate matter, as the sampling particles along with specific structural protections to enable full and natural functionality of contaminant sampling processes on a cumulative basis. One example of such natural cumulative process is that of sampling bacteria, which relies on the process of sediment-based sampling. Sediment-based sampling for fecal contaminants works in this device by having placed a contained volume of sediment or particulate matter (e.g., DE) in the stream, where bacteria may attach and be deposited in said sediment from stream flow. The bacteria can then form a biofilm on the periphery of the sediment column. The DE is retrieved and MFT (membrane filtration test) tested from the particulate material diluted with distilled water, which then represents a sum count after an incubation period for the analysis. These levels of contaminants deposited into the device via any natural cumulative sampling process are dependent on flow-based deposits of contaminants such as bacteria from tributaries, surfaces, and streambeds; however, source and growth-based processes are also more important factors to stream contamination, which are also inherently better observed from a cumulative basis. Cumulative sampling inherently reflects a more total result from these processes of contamination than grab samples, since grab samples provide a single window with limited ability to make inferences until frequent samples are taken. This device in particular also allows for cumulative sampling with bacteria, which "selectively" attach to certain materials opposed to others and appear (given the first observance between frequent grab samples and cumulative samples over the same time period with this device) to have a general preference to attach to specifically this device and the diatomaceous earth material within.

The observances referenced above were from a study in the Commonwealth of Kentucky, which contains the highest mileage of navigable stream waterways in the contiguous United States. This study was conducted to compare the cumulative sampling method with grab sampling. Results raised questions regarding the ability for grab sample based TMDL methods to assess environmentally healthy contaminant levels continuously over time, as such a study would far exceed the EPA's and various States' minimum number of samples and standard guidelines for sampling recreational surface water making it untenable due to cost and time. The frequency of grab sampling from the study was shown to be impractical to expect for any public or environmental health authority to regularly replicate. The study raised questions on if grab sampling methods used alone increased the potential for misdiagnosis of the quality of waterways. In the study, cumulative sampling was shown to reflect total contamination. However, no correlation was found to grab sample values (averages, geometric means, or theoretical sums from estimated integration of a grab sample scatterplot) due to the grab sampling's lack of capability to capture more than single "snapshots" of pollutant levels with grab sampling. The device itself also allowed for better identification of pollutants as point-source or non-point source, and identification of the drivers of non-point source as being tied to eutrophication where cumulative contaminant data was considered alongside algae sampling and regular dissolved oxygen testing in the immediate vicinity of the device.

Grab samples, and past cumulative sampling which have shown no correlation or that risk loss of data from streamflow and particle loss, leave open the question as to how much contamination has truly occurred. In contrast, the cost-effective cumulative water sampling according to embodiments of the present invention may be used to provide an adequate answer. That answer provides knowledge on the cumulative quality of water in the environment over time, relevant to the health of persons interacting with and adjacent to said water, and for assessing indicators of whether that quality is truly healthy for the natural environment on a more wholistic cumulative basis. The cumulative sampling device may also be used in conjunction with grab sampling, at the very least at the placement and retrieval of the device, to allow both knowledge of contamination on a cumulative basis as well as beginning and ending levels of the contaminant. This may also be used for estimates of distribution of the contaminant.

Cumulative sampling with particulate matter is more efficient and cost-effective, and has been proven to be more informative in many cases. The cumulative sampling device and method according to embodiments of the present invention may allow for improved point sourcing where grab sampling is ineffective, an improved standard correlative comparison between watersheds, detection of contaminants missed by other methods, improved ability to regulate and catch acts of pollution without evasion from sampling personnel, and improved ability to understand the distribution of contaminants especially where combined with grab sampling or other instantaneous sampling conducted at least at times of placement and retrieval of the device. The device allows for short intervals of contaminant sampling (e.g., 1 or more hours), or longer intervals (e.g., 30 days, as observed with *E. coli* sampling), which may also depend on the contaminant, flow, and related natural cycles to that contaminant.

In one example, a plurality of the inventive cumulative contaminant sampling devices are placed at various locations of a body of water to collect cumulative contaminant data. Grab sampling is used to collect contaminant data at similar locations at specific points in time. The collected contaminant data can be combined to determine whether any increase or spike in contaminant measurement is local (i.e., caused by contaminant growth in local sediment) or nonlocal (i.e., due to contaminant flow from upstream). This approach may be used to identify locations in the body of water having higher levels of a target contaminant being monitored than other geographic locations and to determine whether the target contaminant increase is due to local growth or contaminant flow from upstream location(s).

The present invention advances the science of contaminant sampling, and does so as a low-cost device making it uniquely accessible to underserved communities and(or) anywhere there is a persistent fecal-indicator bacteria issue and limited resources. The use of fine particulate matter or sediment such as diatomaceous earth (e.g., sterilized DE commonly referred to as Celite®545) enables the absorption of stagnant water column without pumping water in and between particles. It also enables cumulative sampling in lower flow (e.g., flow rates lower than about 5 cfs (cubic feet per second)), and in non-flow when specific embodiments with diatomaceous earth are implemented. For higher flows (or 'flashy' flows often observed in streams in urban areas), the fine particulate matter may be double-bagged in two bags (in one innermost bag within the other) made of a mesh grid of nylon, or equivalent, and housed in a bored housing or bored cannister made of PVC or similar, rigid material. The cannister is not fully perforated. Instead, only one-half lateral side of the cannister is bored with a relatively small number of holes (e.g., 4-10) evenly spaced in varied segments from the top, mid-section, and lower parts of the device. This prevents particle loss to flow and allows an entire column of bagged particulate matter to be compacted and collect contaminants, where in the use of diatomaceous earth as particulate matter the particulate matter may be of finer size in average particle diameter than the size of the mesh bags.

Though parallel orientation to streamflow is desirable by aligning the longitudinal axis of the cannister with the direction of streamflow, where the device can be mounted to a weight, for instance, by tying through the uppermost set of holes, a pocket of air may be present inside the cannister upstream of the bagged particulate matter leading to partial flotation. This has not been observed to affect performance. Of course, other ways of connecting the cannister to a weight may be employed in other embodiments. Tying a weight to the cannister via the uppermost set of holes is merely one example.

FIG. 6 provides an example of the device tied to a sub-surface buoy in perpendicular orientation. The compacting effect by saturated particulate weight, and any flow in stream setting or current, allows for the use of smaller particle size than the mesh size of the double sediment bags (e.g., mesh size equal to or smaller than 75 microns or 200 mesh size) where any flow further compacts the material against the non-bored side of the cannister. For sampling biological contaminants, the mechanical configuration of the device leads to improved consistency of column surface area with smaller sized particles for sampling inside the cannister for biofilm.

According to an aspect the present invention, a sampling device comprises: an elongated tubular body having a longitudinal axis and a hollow interior enclosed at a top longitudinal end and a bottom longitudinal end of the body; a particulate matter; and one or more mesh bags disposed in the interior of the body and configured to contain the particulate matter inside an innermost mesh bag. The innermost mesh bag is contained inside one or more outer mesh bags in a nested configuration when two or more mesh bags are disposed in the interior of the body. The body includes a plurality of body openings on one half lateral side of the body and no body openings on an opposite half lateral side of the body. Though other embodiments of the device are possible, it may be formed and used at an ideal width (or diameter) to length (or height) ratio of 1:4 when used for sampling in water.

In some embodiments, the particulate matter specifically comprises diatomaceous earth (DE). The DE particulate matter used has a median pore size of 12 µm. The one or more mesh bags each have a mesh size of equal to or less than 75 microns.

In specific embodiments, the body openings on the one half lateral side of the body comprise lateral rows of body openings which are longitudinal spaced along the longitudinal axis, each lateral row of body openings includes three openings which are spaced by about 60 degrees (e.g., 60±3 degrees or 57-63 degrees). The body openings on the one half lateral side of the body comprise a plurality of top body openings which are closest to the top longitudinal end of all the body openings. The one or more mesh bags containing the particulate matter, when disposed against the bottom longitudinal end, has an upper portion which is spaced from the top longitudinal end and which is disposed at least partially below the top body openings. In such embodiments, the use of the first or upper group of bored holes may be used for fastening the device with military grade paracord, or other high-tension bearing material, to weights and/or mooring apparatuses. Other embodiments of fastening are possible, so long as the extent of the bored face of the device which covers the bag(s) is not obstructed from the fluid being sampled for contaminants.

In accordance with another aspect of the invention, a sampling device comprises: an elongated tubular body having a longitudinal axis and a hollow interior enclosed at a top longitudinal end and a bottom longitudinal end of the body; one or more mesh bags disposed in the interior of the body and including an innermost mesh bag, the innermost mesh bag being contained inside one or more outer mesh bags in a nested configuration when two or more mesh bags are disposed in the interior of the body; and a particulate matter including DE and disposed inside the innermost mesh bag.

In accordance with yet another aspect of this invention, a particulate-based sampling method utilizes a sampling device which includes an elongated tubular body having a longitudinal axis and a hollow interior enclosed at a top longitudinal end and a bottom longitudinal end of the body. The method comprises: inserting one or more mesh bags inside the interior of the body of the sampling device, the one or more mesh bags including an innermost mesh bag, the innermost mesh bag being contained inside one or more outer mesh bags in a nested configuration when two or more mesh bags are disposed in the interior of the body, the innermost mesh bag containing a particulate matter; and placing the sampling device in a body of water with the top longitudinal end above the bottom longitudinal end or with the top longitudinal end upstream of the bottom longitudinal end.

In some embodiments, the method further includes capturing contaminants from the body of water which are absorbed into spaces between particles of the DE particulate matter or within a volume of the DE particulate matter or both.

In specific embodiments, the method further comprises placing the sampling device in a body of water with the one half lateral side of the body with the body openings above the opposite half lateral side of the body with no body openings. The method may further comprise placing the sampling device in the body of water with the one or more mesh bags containing the particulate matter disposed against the bottom longitudinal end, the one or more mesh bags having an upper portion which is spaced from the top longitudinal end and which is disposed at least partially below the top body openings.

In some embodiments, the method further comprises retrieving the one or more mesh bags from the interior of the body of the sampling device and exposing the particulate matter from the one or more mesh bags; scraping an amount of surface particulate matter from the exposed particulate matter; and weighing the amount of surface particulate matter. The method may further include placing the weighed particulate matter into a first flask, filling the first flask with a first amount of deionized (DI) water, mixing the weighed particulate matter with the first amount of DI water to form a first solution in the first flask, and allowing the first solution in the first flask to settle in place; entering a weighed value of the particulate matter into a bag sediment factor spreadsheet; and calculating a first dilution factor of the first solution based on the weighed value of the particulate matter and a weight of the DI water in the first flask.

In specific embodiments, the method further comprises transferring an amount of the first solution from the first flask to a second flask calculated based on the first dilution factor and mixing the transferred first solution with a second amount of DI water to form a second solution in the second flask; and performing membrane filtration of the second solution for contaminants.

In some embodiments, the method comprises placing a plurality of the sampling devices at a plurality of locations in the body of water to collect cumulative contaminant sampling data at the plurality of locations. The method may further comprise collecting grab sampling data of contaminant at the plurality of locations in the body of water and analyzing contaminant growth in the body of water and source of contaminant growth based on a combination of the cumulative contaminant sampling data and the grab sampling data at the plurality of locations. The method may comprise collecting cumulative sampling data of bacteria using the sampling devices.

BRIEF DESCRIPTION OF THE DRAWINGS

Embodiments of the invention will become more fully apparent from the following detailed description, the appended claims, and the accompanying drawings in which like reference numerals identify similar or identical elements.

FIG. 3B is an exploded view of the bag of particulate matter in the sampling device of FIG. 2.

DETAILED DESCRIPTION

Detailed illustrative embodiments of the present invention are disclosed herein. However, specific structural and functional details disclosed herein are merely representative for purposes of describing example embodiments of the present invention. Though the device itself is also particularly designed to facilitate implementation of diatomaceous earth in cumulative sampling, which yields some particular parts of the design, the present invention may be embodied in many alternate forms as well and should not be construed in any way as limited to only the embodiments set forth herein. Further, the terminology used herein is for the purpose of describing particular embodiments only and is not intended to be limiting of example embodiments of the invention.

As used herein, the singular forms "a," "an," and "the," are intended to include the plural forms as well, unless the context clearly indicates otherwise. It further will be understood that the terms "comprises," "comprising," "includes," and/or "including," specify the presence of stated features, steps, or components, but do not preclude the presence or addition of one or more other features, steps, or components. It also should be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Embodiments of the present invention provide a cumulative sampling device which is configured to compact fine particulate matter that is mesh bagged for sampling. The device is usable in multiple flow regimes and has a higher likelihood for statistic correlation and increased physical durability.

"Cumulative sampling" is the concept of measuring the sum of contaminants over time across a sampling area. This typically occurs where some form of flow is present to transport contaminants through the sampling area or water column. The concept of cumulative sampling holds advantages over more standard grab sampling methods which rely on periodic samples of a water column often to trace contaminants through "point sourcing" or estimate if a contaminant is reaching a regulated total maximum daily load (TMDL). Grab sampling is prone to higher spatial and temporal variability, is more costly, requires more personal or time for sampling site visits, and methods do not consider contaminants attached to sediments or particulate matter.

Figure 1:
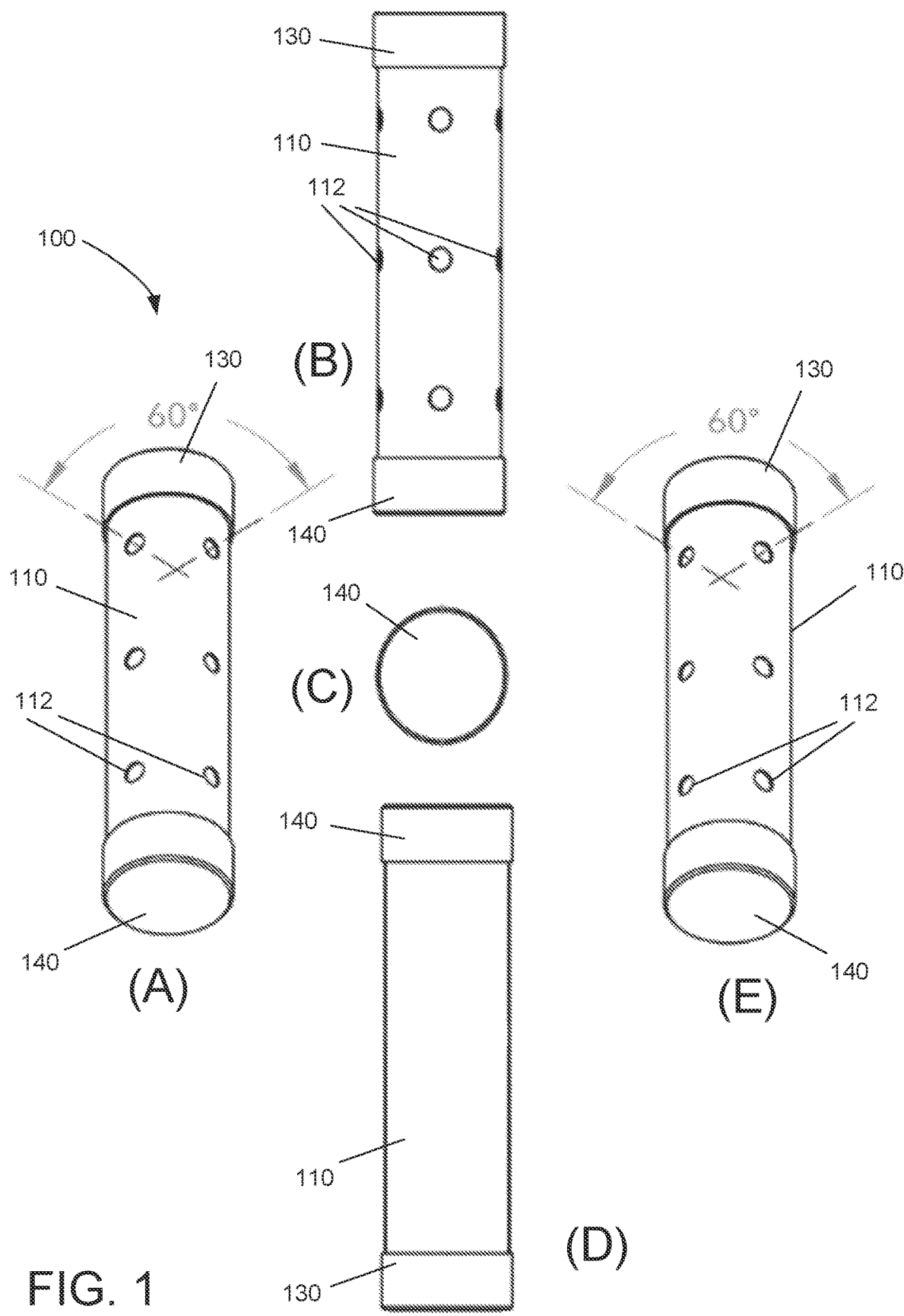
FIG. 1 illustrates an assembled sampling device according to an embodiment of the present invention, including (A) a first perspective view, (B) a front elevational view, (C) a top plan view, (D) a rear elevational view, and (E) a second perspective view thereof.

FIG. 1 illustrates an assembled sampling device according to an embodiment of the present invention, including (A) a first perspective view, (B) a front elevational view, (C) a top plan view, (D) a rear elevational view, and (E) a second perspective view thereof. The sampling device 100 includes a sampling device housing or canister 110 having a plurality of openings 112. The housing 110 has a circular cylindrical shape but may have different shapes in other embodiments. The elongated tubular body of the housing 110 has a longitudinal axis and a hollow interior enclosed at a top longitudinal end and a bottom longitudinal end of the body. The body includes a plurality of body openings 112 on one half lateral side of the body and no body openings on an opposite half lateral side of the body.

In the embodiment shown, the housing 110 has three sets of three holes 112 on one half lateral side of the housing or body 110. There are no holes on the opposite half of the housing 110. The body openings 112 on the one half lateral side of the body comprise lateral rows of body openings 112 which are longitudinal spaced along the longitudinal axis. Each set has a lateral row of three laterally spaced holes 112 which are spaced by about 60 degrees. The three holes 112 include one in the middle and two to the side at about 60° from the middle hole (e.g., 60°±5% or 57° to 63°). The holes 112 may be 0.75 inches. This 0.75 inch diameter may be selected for the use with fine particulate matter such as DE with the mesh size used in the embodiment shown in FIG. 6, where the total surface area of bored holes on the cannister and the volume of particulate matter to be used within that cannister may depend on the length and width of the cannister. The diameter of these holes may be smaller in other embodiments so long as the desired contaminant is not prohibited from entering the device, since it is the intention of the device to allow contaminants to enter the particulate matter to then be sampled from the particulate matter. The diameter of these holes may also be larger in other embodiments where those other embodiments use a different sized mesh or number of bags or otherwise a particulate matter with a larger median pore size than DE (Celite®545). For any embodiment, the angles of the holes and mesh size are not dependent on cannister length and width. The holes in the middle of the cannister may be longitudinally aligned or not aligned. The angular spacing for the holes may be about 45° instead. In other embodiments, the number, spacing, alignment, and arrangement of the holes 112 may change.

The housing 110 may be enclosed by a first end cap 130 and a second end cap 140. In some embodiments, the first end cap 130 may be an upstream end cap or a top end cap and the second end cap 140 may be a downstream end cap or a bottom end cap. The second end cap 140 may be an affixed end cap fixedly attached to the housing 110 and the first end cap 130 may be a removable end cap removably connected to the housing 110. In another example, both end caps 130, 140 are removable. The housing 110 and end caps 130, 140 may be constructed of an inert plastic material such as, for example, polyethylene, polyurethane, or Teflon®.

Figure 2:
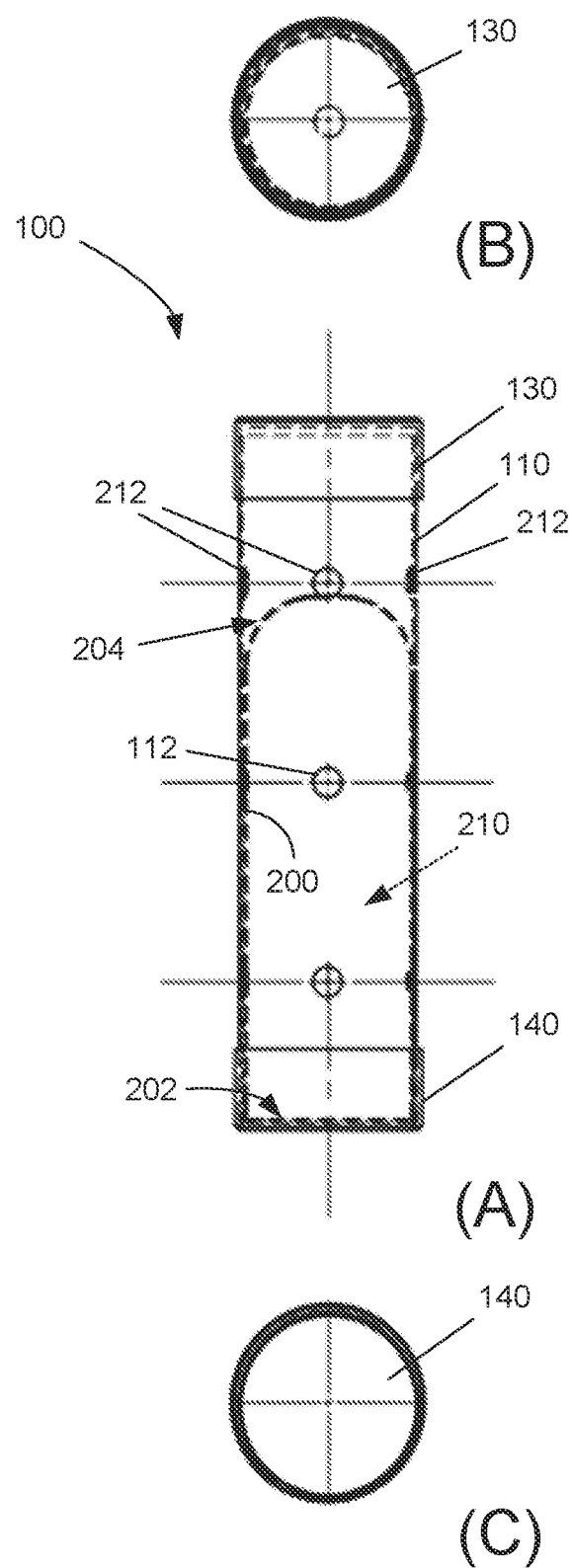
FIG. 2 illustrates the assembled sampling device of FIG. 1, including (A) a front elevational view showing a particulate matter bag in broken lines inside a sampling device housing, a top plan view, and a bottom plan view thereof.

FIG. 2 illustrates the assembled sampling device 100 of FIG. 1, including (A) a front elevational view showing a particulate matter bag 200 in broken lines inside a sampling device housing 110, a top plan view, and a bottom plan view thereof. A particulate matter 210 is disposed inside the bag 200. The bag 200 is shown having a bottom portion or downstream portion 202 pressed against the bottom end cap or downstream end cap (second end cap) 140 and a top or upper portion or upstream portion 204 spaced from the top end cap or upstream end cap (first end cap) 130. A top or upstream lateral row of holes 212, which are closest to the top longitudinal end or top end cap 130 of all the holes 112, are disposed above the top or upper portion 204 or upstream of the upstream portion 204. The upper portion 204 is disposed at least partially below the top body openings or holes 212. The other holes 112 are below or downstream of the top or upstream portion 204 of the bag 200. These top holes or upstream holes allow water to enter and press on the bag 200 of particulate matter 210 toward the bottom or downstream portion 202 against the bottom end cap or downstream end cap 140 at the bottom longitudinal end. FIG. 2 shows the top or upstream lateral row of holes 212 entirely above or upstream of the top or upstream lateral row of holes 212. In other embodiments, the top or upstream lateral row of holes 212 may be only partially above or upstream of the top or upstream portion 204 of the bag 200 (i.e., only some of the top or upstream lateral row of holes 212 are above or upstream, or only a portion of each of the top or upstream lateral row of holes 212, or a mix of both).

Figure 3A:
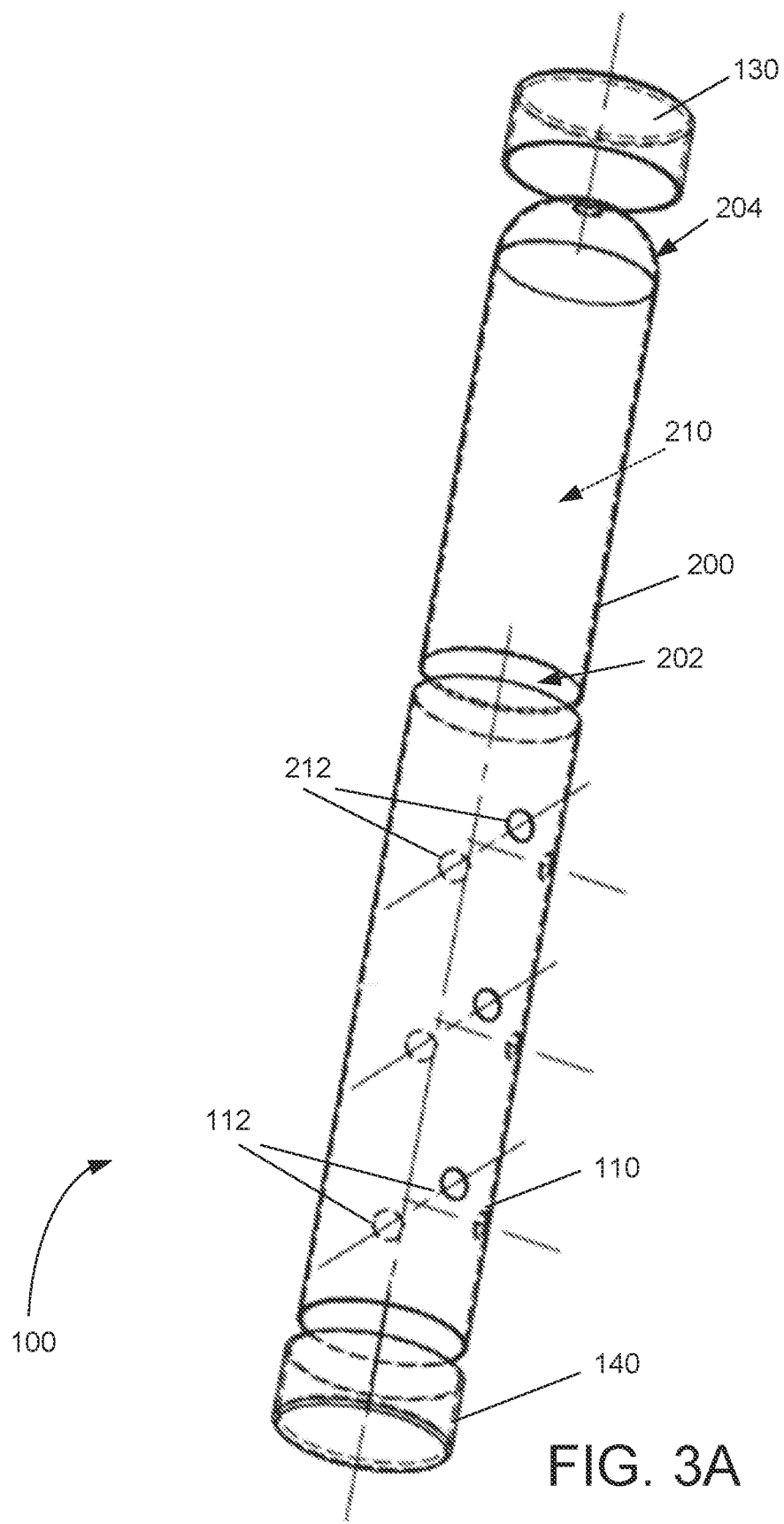
FIG. 3A is an exploded view of the sampling device of FIG. 2.

FIG. 3A is an exploded view of the sampling device 100 of FIG. 2. FIG. 3B is an exploded view of the bag 200 of particulate matter 210 in the sampling device of FIG. 2. One or more mesh bags are disposed in the interior of the housing or body 110 and configured to contain the particulate matter 210 inside an innermost mesh bag 310. The innermost mesh bag 310 is contained inside one or more outer mesh bags 320 in a nested configuration when two or more mesh bags are disposed in the interior of the body 110.

In this embodiment, the particulate matter bag 200 includes two mesh bags 310, 320 nested or double-bagged to contain the particulate matter 210. The mesh bags 310, 320 may have the same mesh size (200 Mesh Size or 75 μm). In other embodiments, the mesh bags may have a different mesh size or have different mesh sizes and there may be more than two nested mesh bags. The mesh bags may be constructed of an inert material such as, for example, nylon or polypropylene. The particulate matter 210 may include fine particulate matter or sediment such as diatomaceous earth (e.g., sterilized DE commonly referred to as Celite®545). The DE particulate matter may have a median pore size of 12 μm.

The sampling device 100 is configured for cumulative sampling or screening of water quality by capturing contaminants over time in a volume of fine particulate material held within the device. The exterior of the particulate matter in the device may also become covered with a biofilm, where biological contaminants may accumulate. Generally, contaminants may be directly deposited into the particulate matter by continuous flow of the fluid in which the sampling device is submerged. They may also be deposited as the sampling device is submerged where a gradient may occur as the fluid is initially absorbed into the spaces between or within the volume of particulate matter inside the device, by introduced hydrostatic pressure forcing the fluid with contaminants into the device, and/or by absorptive properties of the particulate matter held in the device (especially when using diatomaceous earth). The sampling device 100 may capture contaminants from the body of water which are absorbed into spaces between particles of the DE particulate matter 210 or within a volume of the DE particulate matter 210 or both. The volume of particulate matter in the sampling device, which captures contaminants deposited by flow or other means, may be encased by one or more sediment bags (e.g., two cinched nylon bags). In one embodiment, the bags are 8.5×11 inches each when flat, each with mesh size 200 (or 0.75-micron porosity). An estimated volume of 150 cubic inches of particulate matter may be used in the sampling device. The device can potentially be deployed in any natural water source in naturally occurring conditions in a liquid state or similar fluid and conditions.

For use in the environment under multiple flow regimes, one end cap (the affixed end cap 140) may be glued onto the PVC cannister and the other left removable (the removable end cap 130) in order to retrieve the double-bagged particulate matter from the cannister after the desired period of time. This device may be used for short periods of time, one or several days, or up to a month. It could be used for a possibly longer duration so long as the particulate matter does not reach a maximum saturation of the desired contaminant. For use in natural conditions or in a stream, the device may be attached to a mounting apparatus. Mil-spec 550 paracord may be used to tie a bowline knot through two holes on the cannister, to fasten the device to a weight in order to keep the device submerged. The weight may also be tied to surface vegetation. In one embodiment, the PVC cannister has three sets of holes on one half of the cannister face to allow for flow entry and/or fluid absorbance. There are no holes on the opposite half of the cannister. The sampling device is placed in a body of water with the one half lateral side of the body with the body openings above the opposite half lateral side of the body with no body openings. The cannister may be ideally placed lengthwise in any instance of use, such that the face of the holes are parallel to the flow direction. The parallel orientation may be used for higher flows or current of greater than about 15 cfs. If it is turned such that holes are perpendicular, this should not significantly affect results, but may likely require increased mounting weight if used in a stream or fluid flow. The perpendicular orientation may be used for lower flows of less than about 15 cfs, unless implemented in major river systems or ocean setting where mooring to a buoy is required. This too should not significantly affect results— placing the device in perpendicular orientation to the streambed or ocean floor should entail facing the normal direction of the bored side of the device opposing to incoming flow or current as best possible. When used in a stream, the device should be placed in or immediately adjacent to the thalweg. Where higher flows are observed above base flow, the device may be submerged adjacent to the thalweg of the stream or in swirling pools. Scenarios where distribution of cumulative contaminants and spatial variance are a subject of study may warrant the placement of multiple devices in multiple areas in the stream cross-section of study, to be sampled at time intervals as desired.

For analysis after use, it is possible for this device to be sampled for a number of captured contaminants especially if diatomaceous earth is used. This analysis depends on the user's intent. The particulate matter may be analyzed with any procedure for the desired contaminant as it would apply to sediment or saturated sediment material. Saturated particulate samples retrieved from the cannister may also be tested with a similar method to turbid stormwater. To use this method with the device, the submerged specific weight (Ts) of the particulate is determined by dividing dry weight of material by the weight of displaced water, which can be measured as the average of 30 trials pouring water over a known weight of dry particulate inside a tared graduated cylinder until the 100 ml level is reached each trial. With $1rs$ known, an aliquot of saturated particulate of a desired mass can be scraped from the outermost layer of the particulate column retrieved from the device after environmental use. This aliquot may be placed into a tared graduated flask to weigh out the desired mass as it is removed from the particulate column by scraping approximately 1-5 mm deep using a small sterile scalpel. Multiple samples can be tested. Darker coloration along the exterior may be observed along with development of a biofilm. An aliquot sample may be placed in a flask, where DI (deionized) water may then be added until reaching total volume of 100 ml. The initial dilution factor can then be calculated by the equation $1-[1/\gamma s]+[100/\text{Aliquot Weight (g)}]$, and further diluted as desired by the user or analyst. For use in membrane filtration for *E. coli*, or similar method for sampling a biological contaminant that may be attached to particulate matter, any diluted flask may be shaken for 45 seconds and allowed to settle after any dilution. For use with membrane filtration to enumerate colonies (EPA method 1604), some particulate matter may still be present on the filter.

Other possible uses for the sampling device beyond cumulative sampling include contamination profiling especially when paired with grab sampling methods, in order to determine both a cumulative and periodic profile of contamination. This device may also be used to diagnose point-source vs non-point-source contamination. In stagnant water, if the particulate matter in this device was to be "spiked" with nutrient material, this device could potentially be used to attract biological contaminants such as E. coli as they selectively attach to the particulate matter or could estimate nutrient loads based on biological growth responses or other nutrient-dependent factors when compared to a non-spiked control.

In sum, the cumulative sampling device may use a certain type of nylon mesh, specifically with a fine mesh size of 75 microns in some embodiments. It use particulate matter of any particle size but may be optimized for fine particles which other devices cannot use. Some embodiments of the device are specifically designed for use with diatomaceous earth. No induced flow is required to use this device. If implemented to sample the water column, pore sampling devices may not provide accurate samples of the column itself due to spatial and temporal variability from induced flow from a pump, which is also more costly to operate. The current device has lower cost than pore-water sampling devices and provides a truly cumulative sample as opposed to periodic pumping of a pore sampler which may introduce more temporal variability. Although it is possible to deploy the cumulative sampling device or a smaller scale of it into a well or groundwater aquifer for sampling and then retrieve the entire device to test sediment, possibly at lower cost than using pore-water sampling devices in the same well, the primary use of this device is to sample surface water. There is generally more human contact with surface water than ground water along with increased risk of the presence of disease, pathogens, and viruses. Specific embodiments of the device include the use of a bored PVC cannister, use of double bagging, use of finer nylon mesh (200 mesh size or 75 micron), use of fine particle sizes, and novel use of diatomaceous earth, such as sterilized diatomaceous earth (Celite®545) as particulate matter.

The present device for particulate-based cumulative sampling is a significant advancement following previous research which used nylon stocking fabric filled with sediment (construction sand) in certain conditions to sample for contamination such as fecal bacteria contamination. This device is the first to observe statistical correlations with frequent grab sampling. Specific embodiments are optimized for using 700 g of sterilized diatomaceous earth as particulate matter (Celite®545). It has potential application in use for reliable success monitoring of streams, in addition to accomplishing other benefits of particulate based cumulative sampling with improved functionality. Diatomaceous earth has highly absorptive properties and particle porosity that were used to help capture contamination. Although diatomaceous earth is optimal, any particulate matter can be used. Future technological developments may allow for compatibility with remote sensors, or remote deployment and retrieval for analysis of this device.

This device has unique capabilities in sampling for biological contaminants such as fecal-indicator bacteria, over both pore sampling devices and prior sediment bag art. Especially when using diatomaceous earth, both particle pore absorption and the cultivation of a biofilm at the periphery of the particulate column allows for improved cumulative sampling of fecal-indicator bacteria. Diatomaceous earth is unique in the fact that each particle contains a pore channel and allows for water passage both in and between particles, whereas pore sampling is only defined as sampling water in the space between particles. Use of diatomaceous earth is likely not compatible with current pore-water sampling devices due to fine size and risk of particle loss, and possible difficulties as a granular filler.

The cumulative sampling device is usable in multiple flow regimes, with small particle sizes, higher likelihood for statistic correlation, and increased physical durability. Testing has demonstrated the observance of statistical correlation from frequent samples (e.g., high Spearman's Rho in sampling data sets with the device for nonlinear statistical correlations with frequent grab sampling methods).

Measurements of sampling results from this device provided the first known observed statistical correlation with fecal-indicator bacteria in nature between a sediment sample and frequent samples of the stream water column, which is not obtained with any previous sediment-bag or pore-sampling devices.

Regarding the orientation of the canister, it is difficult to achieve the perpendicular orientation. To clarify, that orientation is not necessary to use the sampler in low flow. One study was performed mainly to see if there would be significant magnitude of difference with an adjacent sampling device with parallel orientation to flow (in low flow conditions—which were almost ponded). There was not significant difference. Higher velocities, as those experienced in urban streams, may not allow for perpendicular orientation. In general, the sampling device 100 may be placed in a body of water with the top longitudinal end or top end cap 130 above the bottom longitudinal end or bottom end cap 140, or with the top longitudinal end of top end cap 130 upstream of the bottom longitudinal end or bottom end cap 140.

Figure 4:
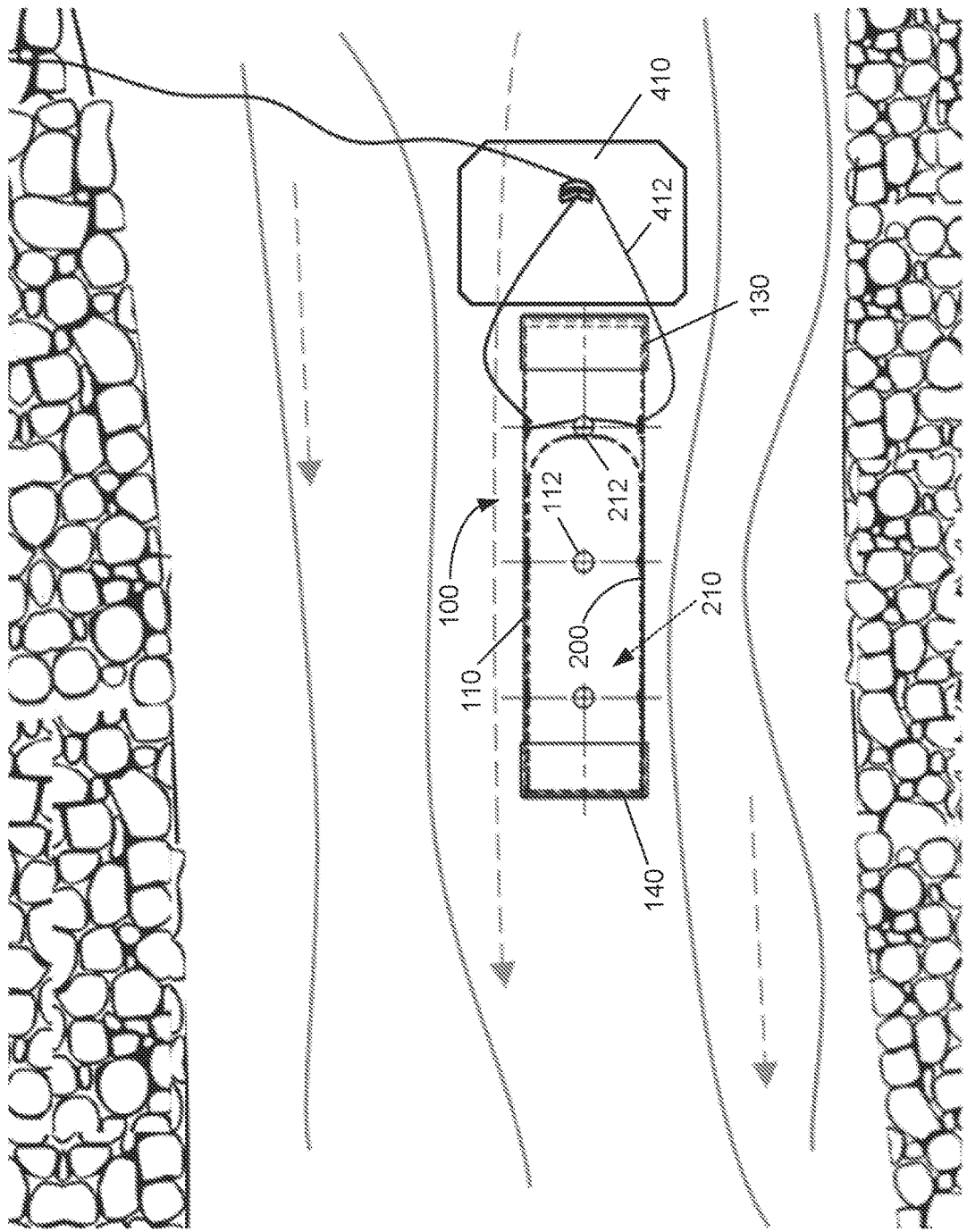
FIG. 4 is an overhead view of a sampling device in streamflow.
Figure 5:
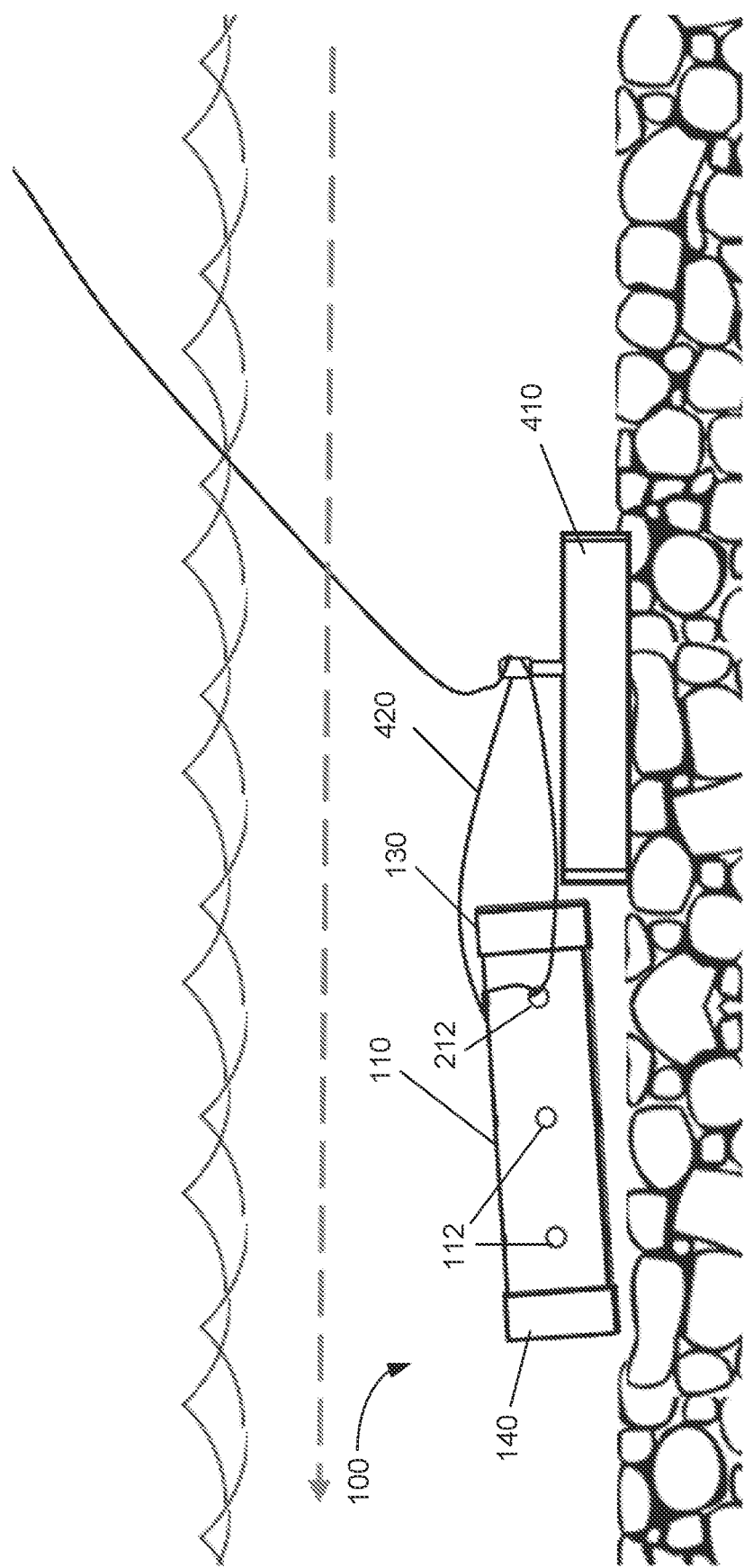
FIG. 5 is a side view of the sampling device of FIG. 4 in streamflow.

FIG. 4 is an overhead view of a sampling device in streamflow. FIG. 5 is a side view of the sampling device of FIG. 4 in streamflow. In this embodiment, the sampling device 100 is generally disposed longitudinally parallel to the streamflow. The top end cap 130 is upstream of the bottom end cap 140. The top end cap 130 may be elevated above the bottom end cap 140.

The bag 200 of particulate matter 210 is downstream of the top or upstream lateral row of holes 212, which are closest to the top longitudinal end or top end cap 130 of all the holes 112. The other holes 112 are below or downstream of the top or upstream portion 204 of the bag 200. These top holes or upstream holes 212 allow water to enter and press on the bag 200 of particulate matter 210 toward the bottom or downstream portion against the bottom end cap or downstream end cap 140 at the bottom longitudinal end. The sampling device 100 may be tied from the most upstream set of holes 212, by the free-form black line 412 representing paracord, to a socket in a concrete weight represented by the rectangular shape 410.

In both illustrations, an additional paracord is tied to the socket in the concrete block and goes from the water onto the shore of the stream. This is for additional safety to avoid losing the apparatus in cases of extreme flow, and allows the apparatus to be tied onto surface vegetation, rocks, or whatever the user of the device may wish to tie the concrete block to.

To avoid unnecessary variation in the methods of use, it can be considered best-practice to use the sampler in parallel orientation to the stream-bed and flow, for any speed of flow. This orientation is also easiest for the device to be mounted to a weight.

Regarding the placement of the sampler 100, in the desirable parallel orientation, it may be considered ideal in any case that it be placed beneath the "thalweg" (center of visible flow lines) in the cross-section of the stream being sampled. If the sampler observes that the current is too strong to allow for safe placement, or otherwise the thalweg's central flow velocity is too great for the weight they are using to mount to the sampler, then it is ideal to place the sampler with that weight immediately adjacent to the thalweg. If in a generally straight section of stream, if the thalweg is distributed more towards one side of the stream, then the sampler should place the device in the side toward which it is distributed. In a stream section with side pools, if it cannot be placed in a thalweg, then it may be placed in those pools where any observed swirling is ideal. When being placed adjacent to the thalweg in a curve, it may be considered ideal to place the device in the outside portion of the curve so the sampler is not skewed by sediment deposition on the inside of the curve. Some sampling personnel may desire to sample on the inside of a stream curve, if it is their desire to capture potential bacteria or other contaminants which may be dislodged in the process of sediment deposition. If doing so, one should watch the device to ensure it is not sedimented into the stream bed or that the holes do not become clogged, especially in streams with finer particulate matter than gravel. Placing a sampler on two sides of a stream curve in that scenario can also allow for a more integrative comparative analysis, where sampling on the outside curve can ensure at least one sampler does not become clogged or sedimented if sampling in larger streams.

Figure 6:
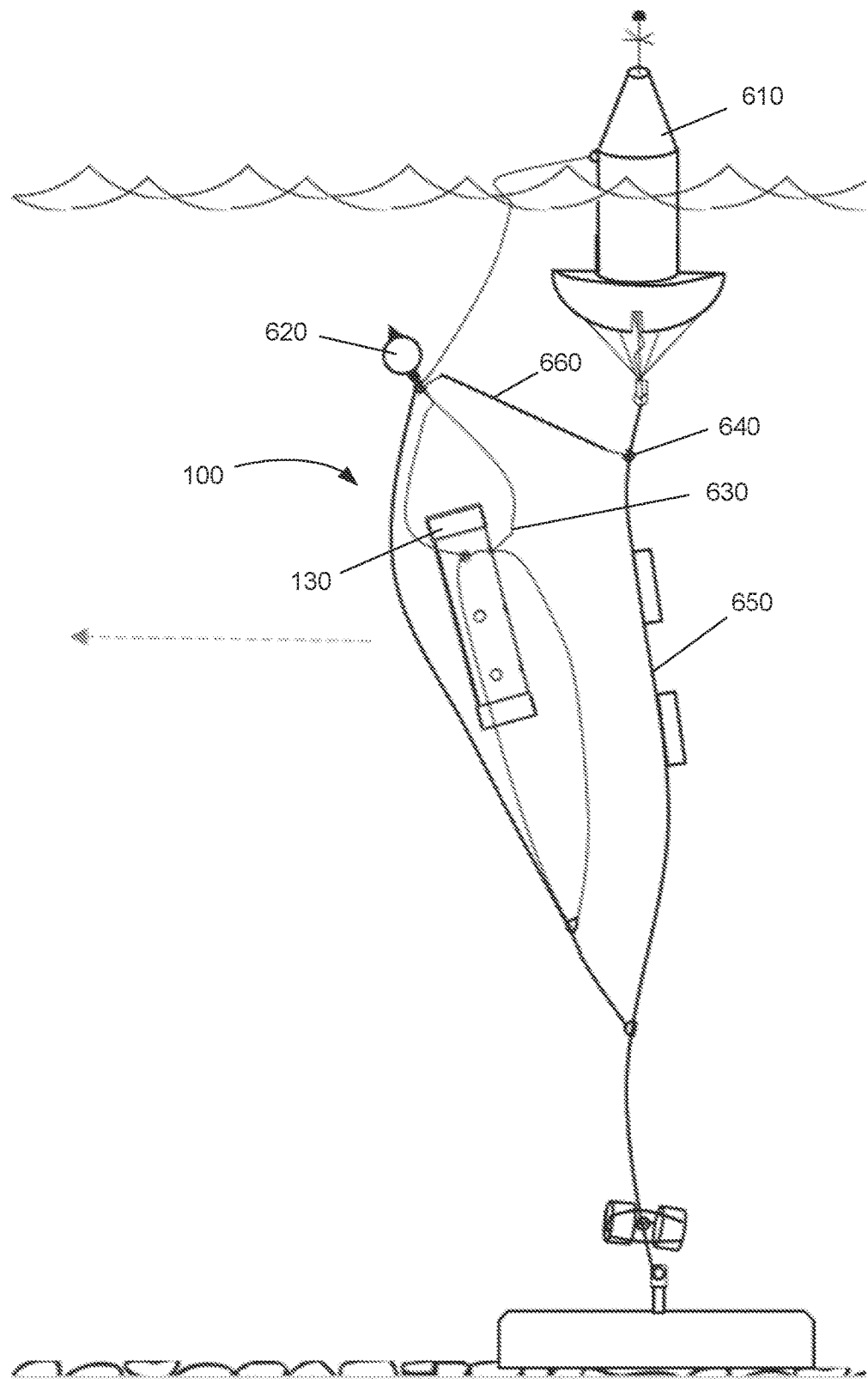
FIG. 6 shows an example of the sampling device fastened to a sub-surface buoy alongside sampling instruments, in a deep navigable river or ocean setting.

FIG. 6 is a side view of the sampling device 100, in context of a deep navigable waterbody or ocean setting such that a navigational or subsurface buoy 610 may be common. An example monitoring apparatus is shown as may be used by the National Oceanic and Atmospheric Administration. The cumulative sampling device 100 is tied to a float 620 from the uppermost set of holes next to top end cap 130, with the sampling device100 disposed latitudinally perpendicular to general current direction of the waterbody in the location of the buoy 610. The device 100 is further tied with rope or mooring line material 630, from the uppermost set of holes most adjacent to cap 130, with line material extending behind the device, and then to a fastener 640 on the weighted mooring line 650 of the buoy 610 which may contain other sampling devices. A non-flexible rod 660 is also shown to create spacing between the device 100 and weighted buoy line 650, other devices, or other mooring lines as to not interfere with the bored surface exposure to the surrounding fluid.

The following describes an example of retrieving and analyzing the collected contaminant samples from the sampling device. After the sampling device 100 is removed from the body of water, the removable end cap 103 is removed, and the bagged particulate matter 210 is taken out of the device. The one or more mesh bags 310, 320 enclosing the particulate matter are removed to expose the particulate matter 210 that generally has been compacted. A first flask may be used for initial dilution of the bagged particulate matter and a second flask may be used for 100-ml dilution to be poured over the bagged particulate matter. A scalpel or scraping device is used to remove samples from the surface of the bagged particulate matter. For example, the sterilized bags (e.g., 75 micron mesh) containing the particulate matter is cut around an annular circle to fit over a glass piece that clamps on the top of the bagged particular matter. One may either clean the cut mesh circle in a bleach bath when finished or, more desirably, use alcohol or denatured alcohol instead, since the alcohol will not degrade the nylon the way that bleach would.

Figure 7A:
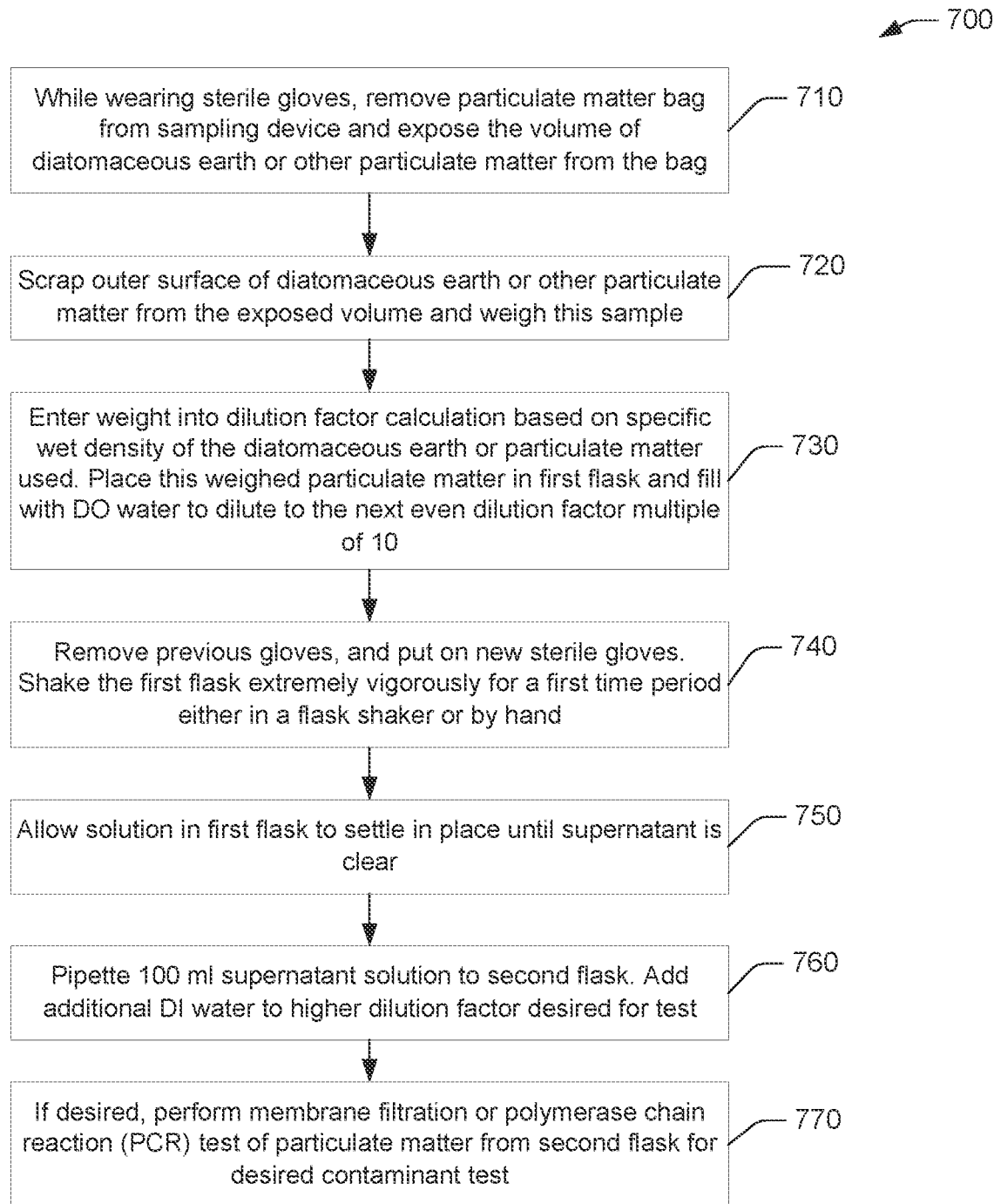
FIGS. 7A-7B show an example of a process for analyzing a contaminant sample from a sampling device, then allowing for further analysis and enumeration of the contaminant by other methods, including membrane filtration or polymerase chain reaction test (FIG. 7A) and Aquagenex Compartment Bag Test and/or Total Coliform Most Probable Number (FIG. 7B).
Figure 7B:
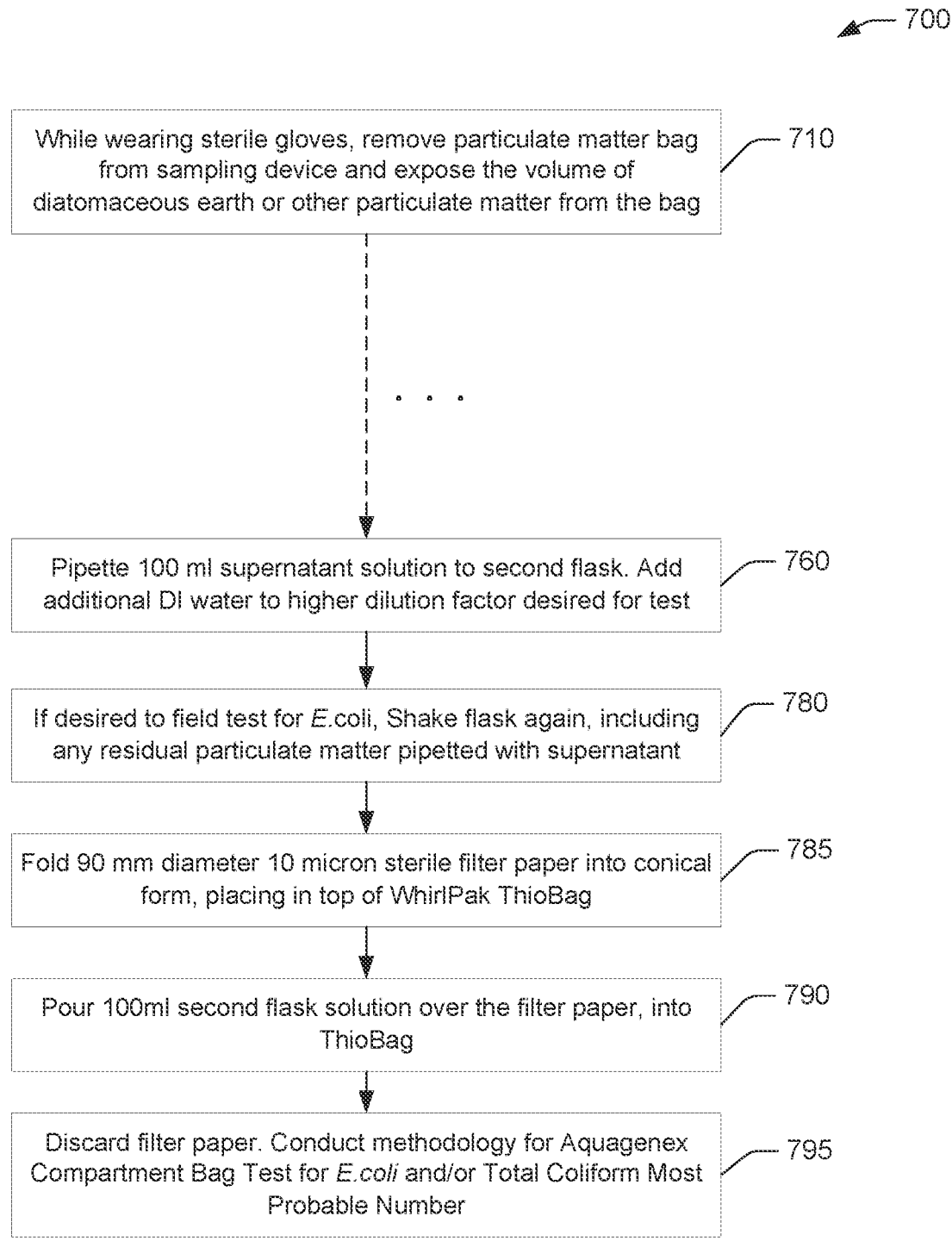

FIGS. 7A-7B show an example of a process for analyzing a contaminant sample from a sampling device, then allowing for further analysis and enumeration of the contaminant by other methods, including membrane filtration or polymerase chain reaction test (FIG. 7A) and Aquagenex Compartment Bag Test and/or Total Coliform Most Probable Number (FIG. 7B).

In step 710 of FIG. 7A, the operator wears gloves and removes the bagged particulate matter from the sampling device. The operator may edge the column of particulate matter out of the mesh bag(s), remove it completely if possible, and set it on a sterile surface such as a sterile Ziploc bag. In step 720, the operator may use a scalpel or a sterile scraping tool to scrap approximately 20 g or more of surface particulate matter onto a weigh plate or scale and record the weight. In step 730, the operator places the weighed particulate matter into the first flask (or sediment flask) and fill it with Di water to the 100 ml mark. In step 740, the operator shakes the first flask extremely vigorously for about 45 seconds to mix the weighed particulate matter with the first amount of DI water to form a first solution in the first flask. In step 750, the operator allows the solution in the first flask to settle in place. Meanwhile, the operator may open the bag sediment factor spreadsheet and enter the weighed value of the particulate matter recorded earlier. The result is the current dilution factor of the solution that was just created based on saturated sediment weight. This first dilution factor of the first solution is calculated based on the weighed value of the particulate matter and a weight of the DI water in the first flask In step 760, the operator calculates the desired dilution, based on the following:

A=initial sediment dilution factor (use the spreadsheet and enter the sediment weight that was recorded; the factor is then usually around 5).

(A)*(B)=nb C, where C equals the desired dilution (i.e., for 1:100, then C is 100). Solve for B.

D=100/B, where D is the volume (ml) of suspended solution in the sediment flask that will be pipetted out and be mixed in the second flask with the DI water (E).

E=100−D, where E is the volume (ml) of DI water to dilute. The operator tares the second flask and measures this value as closely as possible.

The second flask (from E) that was filled with DI and to which the turbid solution was pipetted, is now diluted at the desired dilution factor, C.

The above describes transferring an amount of the first solution from the first flask to a second flask calculated based on the first dilution factor and mixing the transferred first solution with a second amount of DI water to form a second solution in the second flask. In step 770, the operator immediately takes the second flask to the membrane filtration area and sets it down, and prepares for membrane filtration of the second solution for contaminants. Using a rubber band, the operator places the 750 micron nylon circle over the filter apparatus. One or two circles may be used as long as the number is consistent or constant. The operator picks the second flask back up and shakes it extremely vigorously, for instance, for about 45 seconds.

If the operator believes the mesh will catch most of the particulate matter, or if there is little particulate matter, the operator may pour the contents immediately and gradually over the filter apparatus until the entire second flask is empty. This is preferable. On the other hand, if the operator does not believe the mesh will catch most of the particulate matter, the operator may add another sterile mesh circle and then pour it while still turbid. The operator may continue using 2 mesh circles per test. If the operator does not believe having two mesh circles will catch most of the particulate matter, the operator may pour the contents carefully over two of them and try to avoid getting fine sediment onto the apparatus. After pouring the contents, the operator may pipette any remainder. The operator may adhere to the process for all of them, but the second or the first is more preferable. Subsequently, the operator may rinse the nylon mesh circles, clean in alcohol or bleach, dry them.

As an alternative to step 770, FIG. 7B shows steps 780 to 795. In step 780 after step 760, in a process directed to field test for *E coli*, the user shakes the flask again, including any residual particulate matter pipetted with supernatant. In step 785, the user folds a 90 mm diameter 10 micron piece of sterile filter paper into a conical form and placing it on top of a WhirlPak® ThioBag®. In step 790, the user pours the 100 ml second flask solution over the filter paper into the WhirlPak ThioBag®. In step 795, the user discards filter paper and conducts methodology for Aquagenex Compartment Bag Test for *E. coli* and/or Total Coliform Most Probable Number.

Embodiments of the invention can be manifest in the form of methods and apparatuses for practicing those methods.

Unless otherwise indicated, all numbers expressing quantities of ingredients, properties such as molecular weight, percent, ratio, reaction conditions, and so forth used in the specification and claims are to be understood as being modified in all instances by the term "about," whether or not the term "about" is present. Accordingly, unless indicated to the contrary, the numerical parameters set forth in the specification and claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

It will be further understood that various changes in the details, materials, and arrangements of the parts which have been described and illustrated in order to explain embodiments of this invention may be made by those skilled in the art without departing from embodiments of the invention encompassed by the following claims.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

All documents mentioned herein are hereby incorporated by reference in their entirety or alternatively to provide the disclosure for which they were specifically relied upon.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that (1) are enabled by this specification and (2) correspond to statutory subject matter. Non-enabled embodiments and embodiments that correspond to non-statutory subject matter are explicitly disclaimed even if they fall within the scope of the claims.

What is claimed is:

1. A sampling device comprising:
    an elongated tubular body having a longitudinal axis and a hollow interior enclosed at a top longitudinal end and a bottom longitudinal end of the body;
    a particulate matter; and
    at least one discrete, removable bag consisting of mesh material disposed in the interior of the body and configured to contain the particulate matter inside the at least one bag;
    the at least one bag is a first mesh bag;
    the first mesh bag positioned as an innermost mesh bag contained inside one an outer second mesh bags in a nested configuration when two or more mesh bags are disposed in the interior of the body;
    the body including a plurality of body openings on one half lateral side of the body and no body openings on an opposite half lateral side of the body.

2. The sampling device of claim 1,
    wherein the particulate matter comprises diatomaceous earth (DE).

3. The sampling device of claim 1,
    wherein the particulate matter has a median pore size of 12 μm.

4. The sampling device of claim 3,
    wherein the first mesh bag has a mesh size of equal to or less than 75 microns.

5. The sampling device of claim 1,
    wherein the body openings on the one half lateral side of the body comprise lateral rows of body openings which are longitudinal spaced along the longitudinal axis, each lateral row of body openings includes three openings which are spaced by about 60 degrees.

6. The sampling device of claim 1,
wherein the body openings on the one half lateral side of the body comprise a plurality of top body openings which are closest to the top longitudinal end of all the body openings; and
wherein the at least one bag contains the particulate matter, when disposed against the bottom longitudinal end, has an upper portion which is spaced from the top longitudinal end and which is disposed at least partially below the top body openings.

7. The sampling device of claim 1, further comprising:
a top end cap connected to the body to form the top longitudinal end of the body; and
a bottom end cap connected to the body to form the bottom longitudinal end of the body;
at least one of the top end cap and the bottom end cap being removable.

8. A sampling device comprising:
an elongated tubular body having a longitudinal axis and a hollow interior enclosed at a top longitudinal end and a bottom longitudinal end of the body;
a first discrete, removable bag consisting of mesh material disposed in the interior of the body, the first bag is a first mesh bag, the first mesh bag contained inside one or more discrete outer mesh bags in a nested configuration when two or more mesh bags are disposed in the interior of the body; and
a particulate matter including diatomaceous earth (DE) and disposed inside the first mesh bag;
wherein the body includes a plurality of body openings on one half lateral side of the body and no body openings on an opposite half lateral side of the body.

9. The sampling device of claim 8,
wherein the DE has a median pore size of 12 μm.

10. The sampling device of claim 9,
wherein the first mesh bag each has a mesh size of equal to or less than 75 microns.

11. The sampling device of claim 8,
wherein the body openings on the one half lateral side of the body comprise lateral rows of body openings which are longitudinal spaced along the longitudinal axis, each lateral row of body openings includes three openings which are spaced by about 60 degrees.

12. The sampling device of claim 8,
wherein the body openings on the one half lateral side of the body comprise a plurality of top body openings which are closest to the top longitudinal end of all the body openings; and
wherein the first mesh bag contains the particulate matter, when disposed against the bottom longitudinal end, has an upper portion which is spaced from the top longitudinal end and which is disposed at least partially below the top body openings.

13. A particulate-based sampling method utilizing a sampling device which includes an elongated tubular body having a longitudinal axis and a hollow interior enclosed at a top longitudinal end and a bottom longitudinal end of the body, the method comprising:
inserting one or more discrete, removable bags consisting of mesh material inside the interior of the body of the sampling device,
the one or more discrete, removable bags containing particulate matter;
and placing the sampling device in a body of water with the top longitudinal end above the bottom longitudinal end or with the top longitudinal end upstream of the bottom longitudinal end;
wherein the body includes a plurality of body openings on one half lateral side of the body and no body openings on an opposite half lateral side of the body.

14. The method of claim 13, wherein the particulate matter includes diatomaceous earth (DE) particulate matter, the method further comprising:
capturing contaminants from the body of water which are absorbed into spaces between particles of the DE particulate matter or within a volume of the DE particulate matter or both.

15. The method of claim 13, further comprising:
selecting the particulate matter to have a median pore size of 12 μm; and
selecting the one or more mesh discrete, removable bags each to have a mesh size of equal to or less than 75 microns to contain the particulate matter.

16. The method of claim 13 further comprising:
placing the sampling device in a body of water with the one half lateral side of the body with the body openings above the opposite half lateral side of the body with no body openings.

17. The method of claim 13 wherein the body openings on the one half lateral side of the body comprise a plurality of top body openings which are closest to the top longitudinal end of all the body openings, the method further comprising:
placing the sampling device in the body of water with the one or more discrete, removable mesh bags containing the particulate matter disposed against the bottom longitudinal end, the one or more mesh bags having an upper portion which is spaced from the top longitudinal end and which is disposed at least partially below the top body openings.

18. The method of claim 13, further comprising:
retrieving the one or more discrete, removable mesh bags from the interior of the body of the sampling device and exposing the particulate matter from the one or more mesh bags;
scraping an amount of surface particulate matter from the exposed particulate matter; and
weighing the amount of surface particulate matter.

19. The method of claim 18, further comprising:
placing the weighed particulate matter into a first flask, filling the first flask with a first amount of deionized (DI) water, mixing the weighed particulate matter with the first amount of DI water to form a first solution in the first flask, and allowing the first solution in the first flask to settle in place;
entering a weighed value of the particulate matter into a bag sediment factor spreadsheet; and
calculating a first dilution factor of the first solution based on the weighed value of the particulate matter and a weight of the DI water in the first flask.

20. The method of claim 19, further comprising:
transferring an amount of the first solution from the first flask to a second flask calculated based on the first dilution factor and mixing the transferred first solution with a second amount of DI water to form a second solution in the second flask; and
performing membrane filtration of the second solution for contaminants.

21. The method of claim 13, comprising:
placing a plurality of the sampling devices at a plurality of locations in the body of water to collect cumulative contaminant sampling data at the plurality of locations.

22. The method of claim 21, further comprising:
collecting grab sampling data of contaminant at the plurality of locations in the body of water; and analyzing contaminant growth in the body of water and source of contaminant growth based on a combination of the cumulative contaminant sampling data and the grab sampling data at the plurality of locations.

23. The method of claim 21, comprising:

collecting cumulative sampling data of bacteria from each of the plurality of sampling devices;
    wherein each of the collected data is compared to identify what locations within the body of water have greatest concentration of the
contaminant.

\* \* \* \* \*